(12) United States Patent
Boutoussov et al.

(10) Patent No.: US 6,439,888 B1
(45) Date of Patent: *Aug. 27, 2002

(54) OPTICAL SOURCE AND METHOD

(75) Inventors: Dmitri Boutoussov, Dana Point; Colette Cozean, Lake Forest, both of CA (US)

(73) Assignee: PLS Liquidating LLC, Aliso Viejo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,697

(22) Filed: May 3, 1999

(51) Int. Cl.[7] .............................................. A61C 5/00
(52) U.S. Cl. ........................................ 433/215; 433/29
(58) Field of Search ......................... 433/29, 229, 215; 606/13, 14, 17

(56) References Cited

U.S. PATENT DOCUMENTS

| | | | |
|---|---|---|---|
| 5,310,344 A | | 5/1994 | Vassiliadis et al. |
| 5,401,171 A | | 3/1995 | Paghdiwala |
| 5,616,141 A | | 4/1997 | Cipolla |
| 5,634,711 A | * | 6/1997 | Kennedy et al. .......... 433/29 X |
| 5,645,428 A | | 7/1997 | Yarborough |
| 5,752,833 A | | 5/1998 | Yamamoto |
| 5,928,220 A | * | 7/1999 | Shimoji ....................... 433/29 |
| 6,008,264 A | | 12/1999 | Ostler et al. |
| 6,077,073 A | * | 6/2000 | Jacob .......................... 433/29 |
| 6,102,696 A | * | 8/2000 | Osterwalder et al. ... 433/229 X |
| 6,103,203 A | * | 8/2000 | Fischer ..................... 433/29 X |

OTHER PUBLICATIONS

Dental Products Report, High–Speed Curing & Whitening System, DMD Dental/Medical Diagnostic Systems, Inc., Sep. 1998.

Elipar Highlight, Two–step light–curing technology, Brochure, 1997 ESPE America, Inc.

Demetron Kerr, Lighting the Way, Brochure, 1996 Demetron Kerr.

Whitening Teeth: An idea whose time has come, George Freedman DDS, FAACD, FADI, Oral Heath, Mar. 1995, pp. 13–22.

Are Laser Blue Manufacturers with Envy, Special Report: Blue Diode Lasers, Charles T. Whipple, Photonics Spectra, May 1998, pp. 116–125.

Blue Lasers Meet Tough Commerical Requirements, Shuji Nakamura, Special Report: Blue Diode Lasers, Photonics Spectra, May 1998, pp. 130–135.

Arago™ The Right Cure For Your Dental Composites, Brochure, Premier Laser Systems, Inc., Oct. 1995.

Enhancement of Physical Properties of Resin Restorative Materials by Laser Polymerization, Lasers in Surgery and Medicine, vol. 9, No. 6, 1989, pp. 623–627.

\* cited by examiner

*Primary Examiner*—Nicholas D. Lucchesi
(74) *Attorney, Agent, or Firm*—Knobbe, Martens, Olson & Bear LLP

(57) ABSTRACT

An optical device includes a diode light source which is preferably in the form of an array of diode elements such as laser diodes or light emitting diodes (LEDs). The light emitted from the diode elements is directed towards a reflector which directs the emitted light through a heat sink member for controlling the temperature of the diode elements. The heat sink member preferably has a plurality of fins for dissipating heat, and the emitted light passes through these fins and away from the optical device. An optical lightguide may be integrated with the optical device to give the user better control over how the emitted light is imaged. The diode elements preferably emit in either the blue or ultraviolet region of the optical spectrum. In one embodiment of the invention, the output from the diode elements has a cross section that is variable in shape, permitting a composite material within a cavity of a tooth to be cured in such a way that microgaps between the tooth and the composite are not formed.

7 Claims, 8 Drawing Sheets

OPTICAL SOURCE AND METHOD

BACKGROUND OF THE INVENTION

1. Field of the Invention

The present invention relates to a compact source of optical radiation.

2. Description of the Related Art

Since its invention some 30 years ago, the laser has found a wide variety of applications. Despite their versatility, lasers themselves are often difficult to work with because of their size. Current light sources for producing laser light or other intense optical radiation, whether they be for curing or cutting, are frequently not sufficiently compact for hand-held operation. Additionally, they typically require an electrical hookup, and in general, are not battery operated. Fields which require compact, relatively high intensity light sources are dentistry and surgery. In particular, dentists use light for curing resins and composites in the mouth, and also the bleaching of teeth. For optimum results, these applications typically require intense emission in the blue region of the optical spectrum. However, intense blue light sources are generally not available in a compact hand-held unit that is easy to manipulate within an oral cavity. Further, in the case of curing composites in a cavity in a tooth, the curing process generally leads to the formation of microgaps between the tooth and the cured composite material within the cavity.

Recent advances in semiconductor technology relating to laser diodes and light emitting diodes (LEDs) have enabled the miniaturization of light sources. However, these semiconductor devices often do not generate high power, and in general, thermal management is a problem for compact, high power devices.

Thus, there remains a need for a compact, intense source of optical radiation which can be used in dentistry or in other fields involving close working quarters.

SUMMARY OF THE INVENTION

According to one aspect of the invention, an optical device includes a diode light source for emitting light, a heat sink member that is in thermal contact with the diode light source, a reflector for receiving the emitted light (in which the reflector directs the emitted light towards and through the heat sink member, and away from the reflector), and a housing for securing the diode light source, the heat sink member, and the reflector. The heat sink member preferably includes a tapered base in thermal contact with the diode light source, and also a plurality of fins in thermal contact with and extending away from the base, so that the fins conduct heat away from the base. In a preferred embodiment of the invention, an optical element such as a lightguide is used for directing the emitted light away from the optical device. In one preferred embodiment of the invention, the diode light source emits blue light, and in another, ultraviolet optical radiation.

Another aspect of the invention comprises a method of providing intense optical radiation, in which the method includes providing a diode light source that emits light, using a heat sink member to stabilize the temperature of the diode light source, directing the emitted light towards a reflector, and reflecting the emitted light from the reflector towards and through the heat sink member, and away from the optical source. In a preferred embodiment, the emitted light is directed onto an optical lightguide.

According to another aspect of the invention, an optical device includes a penlight shaped housing, a diode light source which emits blue light (in which the light source is mounted within the penlight housing), and an optical lightguide connected to the penlight housing which receives the blue light, wherein the optical lightguide is configured to provide a curved light path suitable for use in an oral cavity.

Another aspect of the invention comprises a method of tooth whitening, in which the method includes applying a tooth whitening material to a tooth, allowing the tooth to be exposed to the material in the absence of activating light for a substantial period of time, utilizing an array of diodes to produce activating light having a wavelength in the range 400–600 nm, and applying the activating light to the material at a power level of 100–600 mW for a period of 20–40 seconds. In one preferred embodiment, the application of the activating light is terminated before the tooth receive 14 Joules of laser energy during any one application of the activating light.

Yet another aspect of the invention comprises a method of treating a tooth, in which the method includes applying a dental composite or resin material to a tooth, utilizing an array of diodes to produce activating light having a wavelength in the range 400–60 nm, and applying the activating light to the dental material at a power level of 100–200 mW for a period of 2–5 seconds.

Yet another aspect of the invention comprises a method of treating teeth at a plurality of dental treatment stations, in which the method includes delivering power from a single power supply through a plurality of power lines to respective dental stations, utilizing power from each of the power lines to energize a diode light source to produce light in the optical range of 400–600 nm, applying a light sensitive material to a tooth of a patient at a first treatment station and exposing the material to light in the optical range of 400–600 nm, and applying a light sensitive material to a tooth of a patient at a second treatment station and exposing the material to light in the optical range of 400–600 nm. In one preferred embodiment, the method further includes applying a light sensitive material to a tooth of a patient at a third treatment station and exposing the material to light in the optical range of 400–600 nm. In a preferred embodiment, the light sensitive material is selected from the group consisting of a tooth whitening material, a dental composite material, and a dental resin.

According to one aspect of invention, a medical apparatus includes an array of optical sources, and a housing to which the array is mounted, wherein the optical sources are connectable to a power supply and individually addressable to produce at least two different output intensity patterns, and wherein optical output from the optical sources can be directed onto tissue by orienting the housing by hand. In one preferred embodiment, the array produces an annulus of optical radiation. In another preferred embodiment, the light emitted from the diode light source is absorbed by teeth.

Another aspect of the invention comprises a method for use on a tooth having a cavity that is at least partially filled with a dental composite, so that the composite contacts the tooth tissue that forms the cavity, in which the method includes providing a first optical beam having an intensity distribution in cross section that concentrates energy at the periphery of the cross section, using the first optical beam to cure the composite contacting the tooth tissue at the sides of the cavity without curing composite that is interior of the cavity, providing a second optical beam having an intensity distribution in cross section that does not concentrate energy at the periphery of the cross section, and curing the composite within the interior of the cavity with the second optical beam. In a preferred embodiment, the optical beams are transmitted sequentially through an optical lightguide.

Another aspect of the invention comprises a method, in which the method includes utilizing an optical source to produce an optical beam with a cross section having a first intensity pattern, utilizing the optical source to produce an optical beam with a cross section having a second intensity pattern different from the first intensity pattern, transmitting the optical beams along a common optical path to a target area without substantially varying the respective patterns of the cross section, grasping the optical source in a hand of a user, moving the user's hand to position the optical source, and directing the optical beams onto the target area. In a preferred embodiment of the invention, the target area comprises tissue, such as tooth tissue.

According to another aspect of the invention, a dental apparatus for use on a tooth having a cavity that is at least partially filled with a dental composite (so that the composite contacts the tooth tissue that forms the cavity) comprises means for producing a first optical beam having an intensity distribution in cross section that concentrates energy at the periphery of the cross section, means for producing a second optical beam having an intensity distribution in cross section that does not concentrate energy at the periphery of the cross section, and means for directing the first and second optical beams towards the tooth, in which the first optical beam cures the composite contacting the tooth tissue at the sides of the cavity without curing composite that is interior of the cavity, and the second optical beam cures the composite within the interior of the cavity.

Another aspect of the invention comprises a method of curing an optically curable material filling in a tooth, including using optical energy to cure filling material that is adjacent to tooth tissue at a periphery of the filling prior to curing filling material that is interior to the periphery.

DETAILED DESCRIPTION OF THE PREFERRED EMBODIMENT

Figure 1A:
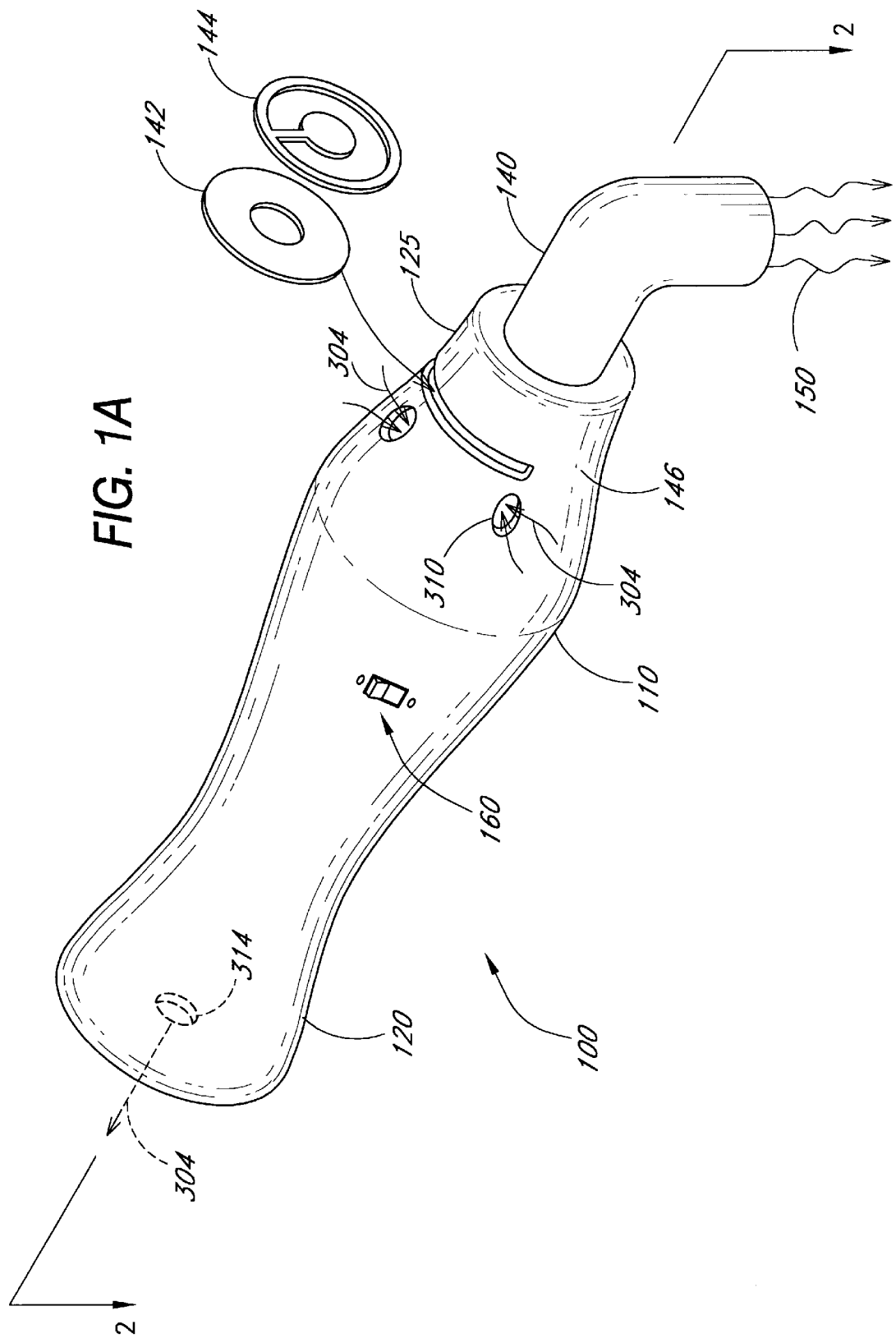
FIG. 1A shows a perspective view of one embodiment of the invention, a hand held optical device.

As shown in FIG. 1A, the preferred embodiment of the invention comprises a hand held optical device 100, preferably less than about 20 cm long which provides a compact structure that can be used to conveniently deliver intense optical radiation, such as laser radiation, to locations which would otherwise be difficult to reach. The user grasps the optical device 100 with his or her hand, and moves his or her hand to properly orient the light. For example, the optical device 100 may be used in medical (e.g., surgical) procedures or to cure light sensitive material located in tight quarters, such as glue sandwiched between components. Also, the device 100 may be used in blood coagulation procedures, in which the energy density of the optical radiation delivered onto the blood is advantageously greater than about 10 J/cm$^2$. The optical device 100 comprises an elongate, penlight-shaped housing 110 having a proximal handle portion 120 for aiming the optical device 100, and a distal receptacle portion. A receptacle 125 in the distal portion has an opening which receives and mates with a probe formed by an adaptor 130 and an optical element such as an optical lightguide 140, although this optical element may also include other optical components such as lenses and filters for changing the direction of optical radiation or altering its profile. The bottom of the receptacle 125 comprises a protective, optically transparent window 127. The length of the adaptor 130 is approximately equal to the depth of the receptacle 125 so that the adaptor is disposed substantially entirely within the receptacle 125. The optical lightguide 140, one end of which is mounted in the adaptor 130, extends from the window 127 to a location which is distal of the housing 110. The lightguide 140 is preferably curved so as to direct light output from the optical device 100 transversely to the longitudinal axis of the handle portion 120. For example, the optical lightguide 140 may be configured to provide a curved light path suitable for use in an oral cavity, and may comprise a few hundred fiber optic strands capable of providing image transfer quality. The adaptor 130 snaps into and off of the receptacle 125 of the housing 110. Thus, the housing 110 can be used with various waveguides or optics of different configurations and functionality. The device 100 may optionally include an optical mask 142 or 144 for controlling the pattern of optical radiation 150 emitted by the device, as discussed in greater detail below.

Figure 2:
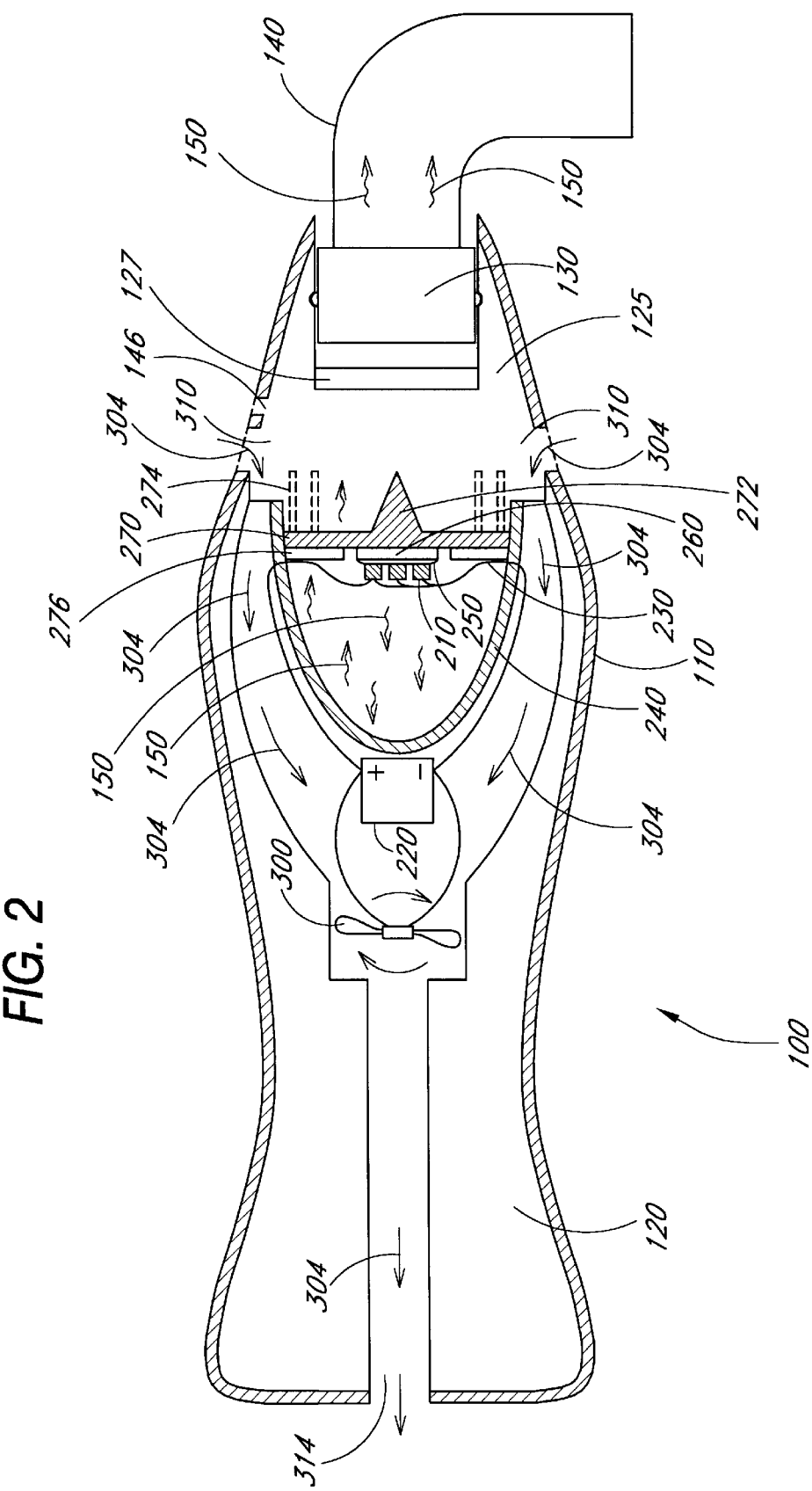
FIG. 2 shows a cross sectional view of the embodiment shown in FIG. 1A.
Figure 3:
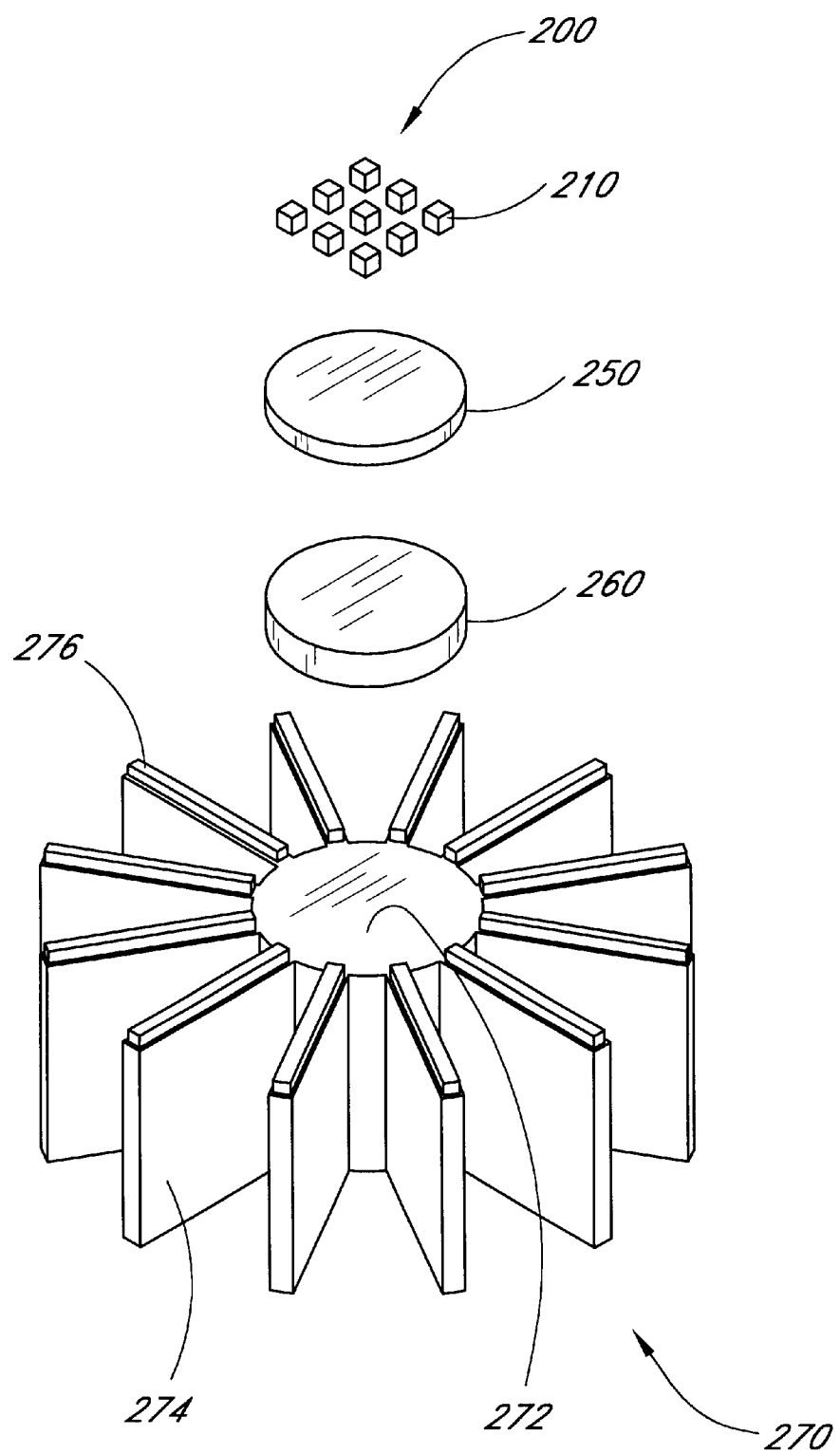
FIG. 3 is an exploded view of several optical components and a heat sink member which form part of the embodiment shown in FIGS. 1A and 2.
Figure 4:
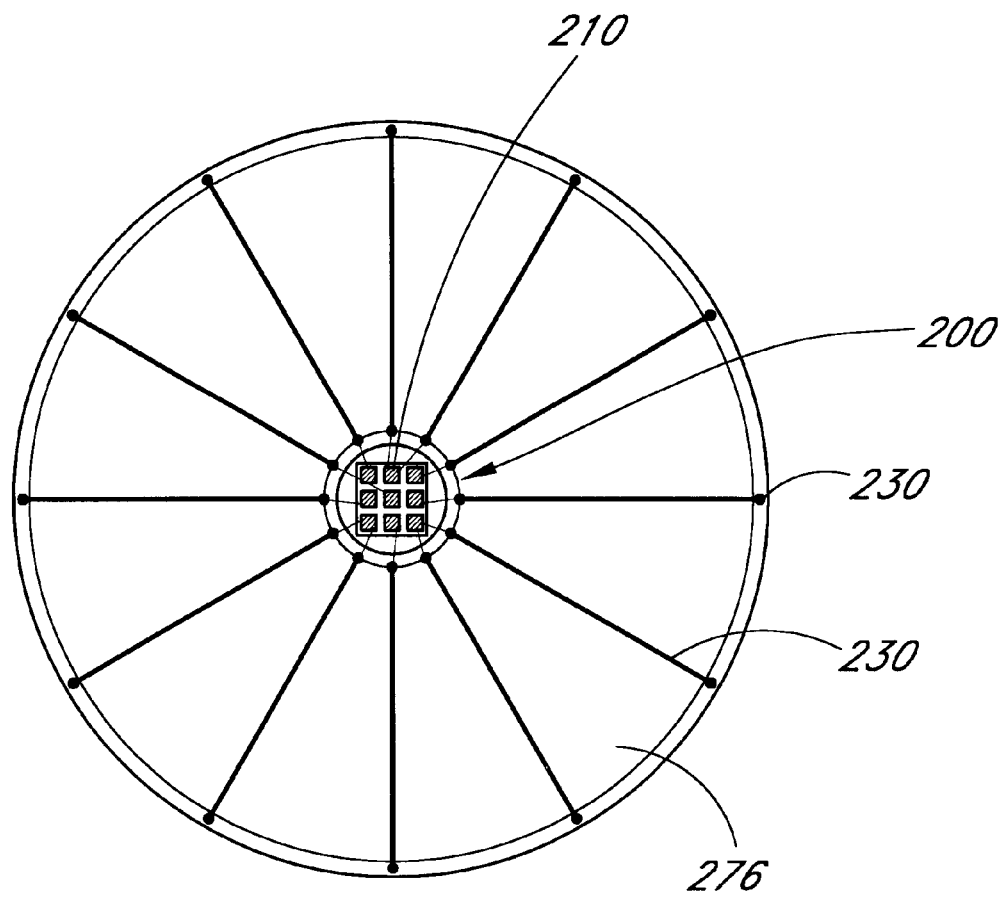
FIG. 4 is a plan view of an LED array resting on the base of the heat sink member of FIGS. 2 and 3.

Referring to FIGS. 2–4, the hand held optical device includes a light source 200. The preferred embodiment 100 comprises an array of diode elements 210 comprised of light emitting diodes (LED) or laser diodes, although the light source 200 may alternatively comprise a single (non-array) crystal. The diode array 210 is comprised of a semiconductor material, such as GaN, tailored for a portion of the optical spectrum between 300 and 650 nm and collectively may produce from 2 to 1000 mW of output. In one preferred embodiment, the diode elements 210 emit in the ultraviolet (UV) portion of the spectrum at 365±30 nm. This wavelength regime is suitable for curing glues, such as those used for holding optical components together. In another preferred embodiment, the diode elements 210 emit blue light at 468±10 nm, which is a spectral regime suitable for chemically activating camphorquinone, which absorbs at these wavelengths. This compound is a catalyst in dental composite materials such as Silux (3M), Bifsil (Bisco), and Aelitefil (Bisco). Blue light also overlaps the absorption spectrum of catalysts in dental resins, and is useful in various tooth whitening procedures, since blue light is effectively absorbed by color centers in teeth. This absorption by color centers leads to localized heating within teeth and thus more efficient activation of whitening compounds such as hydrogen peroxide.

The GaN diode elements 210 may be obtained commercially from Nichia Chemical Industries (Tokyo, Japan). The individual diode elements 210 are generally 50 to 500 microns in diameter (or in length, if they are square), and may be placed closely together or separated from each other by up to about 150 microns. The diode elements 210 are preferably arranged in an array, which may, for example, be a 6×6 array of 36 elements, or as few as 9 elements arranged in a 3×3 array. The array that forms the diode light source 200 is preferably no larger than one square inch. As illustrated in FIG. 2, one or more electrical contact lines 230 for delivering power connect the diode elements 210 to a power supply 220, such as a battery (which may reside within the housing 110 and is connected to an on/off switch 160) or an AC power supply. If a battery is used, it is preferably a rechargeable lithium or nickel cadmium battery of about 1–3 amp-hour capacity. A plurality of electrical contact lines 230 provide an electrical path from the battery or AC power supply to the array, as shown in the 3×3 array of FIG. 4, although just one pair of lines is shown in FIG. 2 for the sake of clarity. The diode elements 210 may have a common electrical return line (i.e., a single one of the contact lines 230 in FIG. 4). Providing the diode elements 210 with several electrical supply lines (rather than just one) facilitates stable delivery of current to the diode elements, which is important when the output from the diode elements should be in a specific, stable intensity pattern. The electrical contact lines 230 pass through a reflector 240 which receives the optical radiation 150 emitted by the diode light source 200. In the embodiment of FIG. 4, the array is formed of LEDs and thus, the emission 150 occurs from the bottom surfaces as well as the top and side surfaces of the LEDs.

A substrate 250 that is preferably sapphire (semiconductor materials may also be suitable) underlies the LED array 200. The individual LED elements 210 may located on a common substrate 240, or each element may have its own substrate. A reflecting element 260 in turn underlies the substrate 250 and reflects light 150 emitted from the bottom surfaces of the LEDs 210 back towards the reflector 240. The reflector 240 is contoured to focus light into the optical lightguide 140. By way of example, e.g., the reflector may be ellipsoidal in shape. The reflecting element 260 may be a separate optical component, a coating on the substrate 250, or a coating on the base 272.

A heat sink member 270 is positioned at the mouth of the ellipsoidal cavity formed by the reflecting element 260. The heat sink member 270 is in thermal contact with the diode light source 200, and conducts heat away from the diode light source 200, thereby controlling and stabilizing its temperature and facilitating stable power output and better efficiency from the diode light source. The heat sink member 270 preferably includes a solid tapered base 272 and a plurality of fins 274 which dissipate heat by conducting it away from the base. As shown in FIG. 3, the fins 274 extend radially outward from the base 272 and preferably extend radially beyond the reflector 260. Each of the fins 140 lies in a plane substantially parallel to the longitudinal axis of the handle so that the fins do not block the reflected light. The fins 274 may advantageously be from 0.2–1 mm thick, and from 1 to 50 fins may be used. The heat sink member 270 is preferably a high thermal conductivity material such as copper, silver, brass, aluminum or stainless steel. The heat sink member 270 is insulated from the electrical contact lines 230 by a thin layer of insulating foil 276 such as plastic. The foil 276 may be in the form of thin, long narrow strips that separate the fins 274 and the contact lines 230 as shown in FIG. 3. Alternatively, the foil 276 may be a continuous sheet that rests over and extends between the fins 274 with the contact lines 230 resting on the foil, as in FIG. 4, in which case the foil is transparent to allow passage of the emitted light. Alternatively, the electrical contact lines 230 may each have a plastic sheath surrounding them to provide insulation.

Light 150 emitted from the diode light source 200 is directed by the reflector 240 towards and through the heat sink member 270, and in particular, through openings between the fins 274 of the heat sink member. The fins 274 are preferably reflective at the wavelength of the emitted light 150 so that any light rays incident thereon will be efficiently reflected without significant attenuation. The surfaces of the fins 274 may be coated, for example, with silver or aluminum to increase their reflectivity. The geometrical relationship between the heat sink member 270, reflecting element 260, the substrate 250, and the diode elements 210 is shown more clearly in the exploded view of FIG. 3.

The various components within the housing 110, including the diode light source 200, the heat sink member 270, and the reflector 240 may be held in place using clamps, fasteners, or other mechanical devices (not shown in the Figures), as is known in the art. As shown most clearly in FIG. 2, the diode light source 200, the heat sink member 270, and the reflector 240 are mounted in a cavity formed in the forward portion of the handle, adjacent the receptacle 125.

To aid in thermal management, a fan 300 may be optionally included in the housing 110 and may advantageously be powered by the power supply 220. The fan 300 is mounted in a cavity in the handle 120, rearward of the reflector 240. When energized, the fan 300 draws in air 304 through one or more air intake ports 310 and directs the air across the fins 274 of the heat sink member 270 and past the reflector 240. The air 304 exits the device 100 through an air exhaust port 314.

The optical lightguide 140, such as a fiber optic bundle, receives the emitted light 150 from the reflector 240 and guides the emitted light to an output end of the lightguide 140. The optical lightguide 140 allows the user to direct the emitted light into areas that would otherwise be hard to reach. The user grasps the optical device 100 with his or her hand, and moves his or her hand to properly orient the light onto a target area. For example, the optical lightguide 140 may be used to direct emitted light 150 onto the tooth of a patient in a tooth whitening procedure.

Figure 1B:
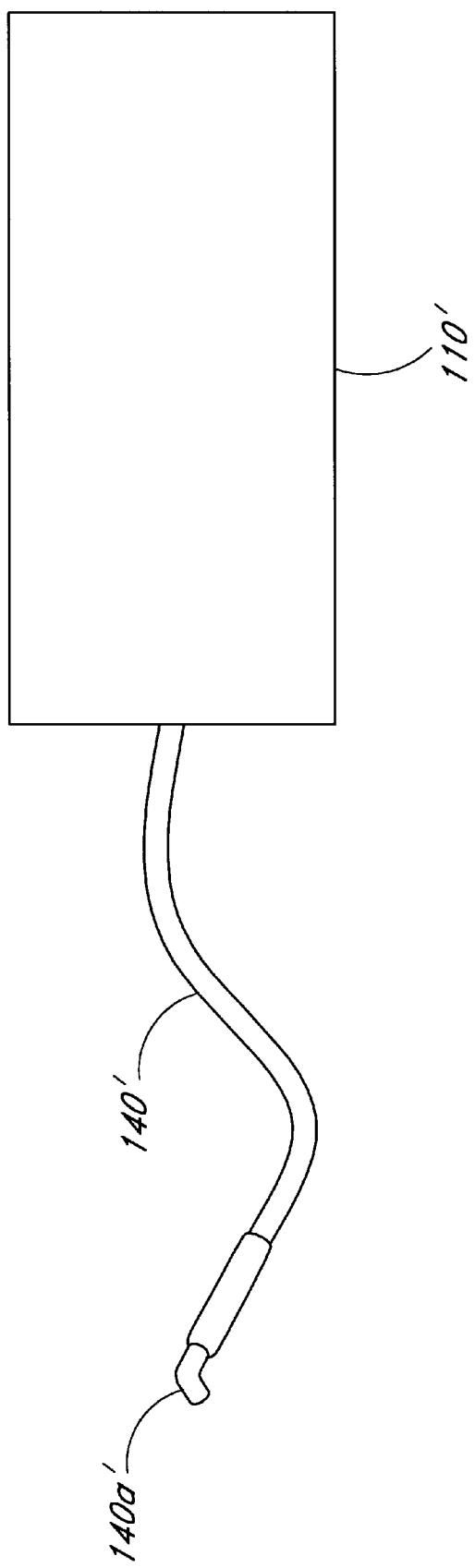
FIG. 1B shows a schematic view of an alternative embodiment in which a relatively long optical lightguide is used to deliver optical radiation to a target area.

An alternative embodiment is illustrated in FIG. 1B, in which the diode elements 210, the reflector 240, and the heat sink member 270 are all contained within a housing 110', which may be positioned on a table, for example. In this case, the optical lightguide 140' may be a meter or more in length. The distal end 140a' of the optical lightguide 140' may be advantageously curved (like its counterpart optical lightguide 140) to permit the user to direct light around corners or into areas that are hard to access. In this embodiment, the user manipulates the distal end 140a' of the lightguide 140' rather than the entire device.

The optical device 100 may be advantageously used in an office setting having more than one dental treatment station (not shown), with only one power supply (not shown) being used to supply power to one or more of the optical devices. Power may be delivered from the power supply through a plurality of power lines (not shown) to respective dental stations. One or more of the power lines may be 8 feet long or longer. Power from each of the power lines may then be utilized at the respective dental stations to energize the diode light source 200 (e.g., the diode array 210) within the optical device 100 to produce light in the optical range of 400–600 nm, e.g., blue light. A light sensitive material (such as a tooth whitening material, a dental composite material, or a dental resin) may be applied to a tooth of a patient at a first treatment station and then exposed to the light from the diode light source 100. This procedure may then be repeated on the teeth of other patients at second or third (or more) dental stations. This method saves the expense of dedicated power supplies for each of the dental stations, and may be used in conjunction with any of the dental procedures disclosed herein.

The optical device 100 may be used in other dental procedures as well, such as the composite curing method described herein, which avoids the formation of microgaps between a tooth and cured composite material within a cavity in that tooth. To this end, the generation of beams of light having circularly and annularly shaped cross sections is desirable, as discussed below. More generally, a first beam has an intensity distribution that concentrates energy at the periphery of its cross section, whereas a second beam does not concentrate energy at the periphery of its cross section, for example, the intensity of the second beam is concentrated closer towards the center of the cross section, or the intensity of the second beam is evenly distributed over the cross section.

Figure 5A:
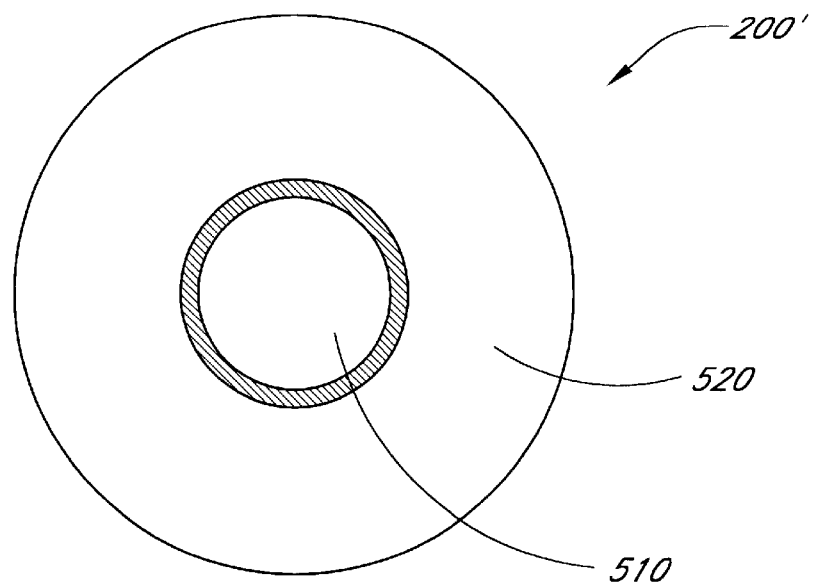
FIGS. 5A and 5B illustrate two preferred configurations of the light source used in the hand held optical device.

As shown in FIG. 5A, the diode light source 200' of this embodiment (which may replace the light source 200 of FIGS. 3 and 4) may advantageously comprise concentric diode elements 510 and 520, in which either one or both of the diode elements 510 and 520 may be turned on at any one time. Thus, if the diode element 510 alone is activated, the light source 200' generates an optical beam that has a circularly shaped cross section. On the other hand, if the diode element 520 alone is activated, the optical beam generated by the light source 200' has an annularly shaped cross section. If both diode elements 510 and 520 are turned on, then the optical output has a circularly shaped cross section. Thus, the cross section of the light source 200' is variable between first and second patterns.

Figure 5B:
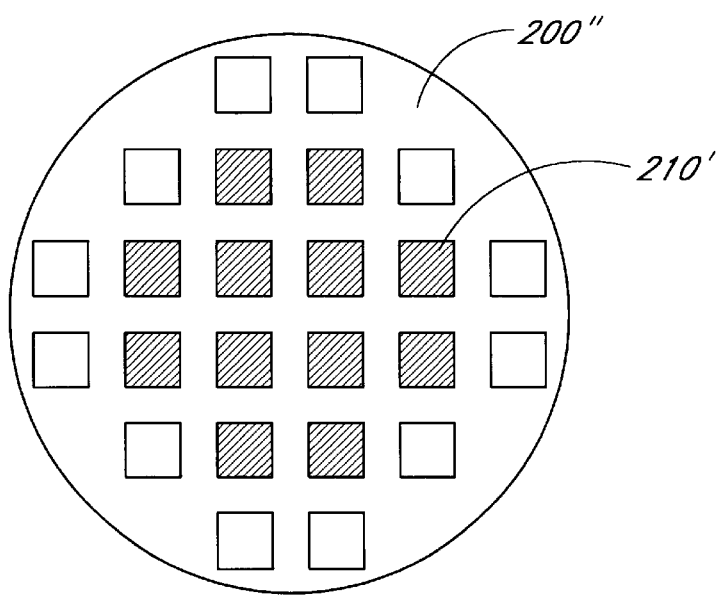

Alternatively, optical beams with circularly and annularly shaped cross sections may be generated with a diode light source 200" like that illustrated in FIG. 5B, in which the light source 200" (like its counterpart 200) comprises an array of diode elements 210'. For example, by activating diode elements 210' near the center of the array (the darkened elements in FIG. 5B), optical output having a cross section that approximates a circle can be generated. Likewise, by activating diode elements 210' closer to the periphery of the array (the undarkened diode elements in FIG. 5B), the optical output that is generated has a cross section that approximates an annulus. By using a greater number of diode elements 210', a desired intensity profile can be approximated more accurately. In each of the embodiments of FIGS. 4, 5A, and 5B, the diode elements are located at positions (within the housing 110) that are fixed with respect to each other, and further, each of the diode elements is individually addressable, being connected to a power supply via electrical contact lines 230 (not shown in FIGS. 5A and 5B). The output from the light source 200, 200', or 200" can be directed onto tissue (e.g., hard tissue such as a tooth) by properly orienting the housing 110 of the optical device 100.

Figure 6A:
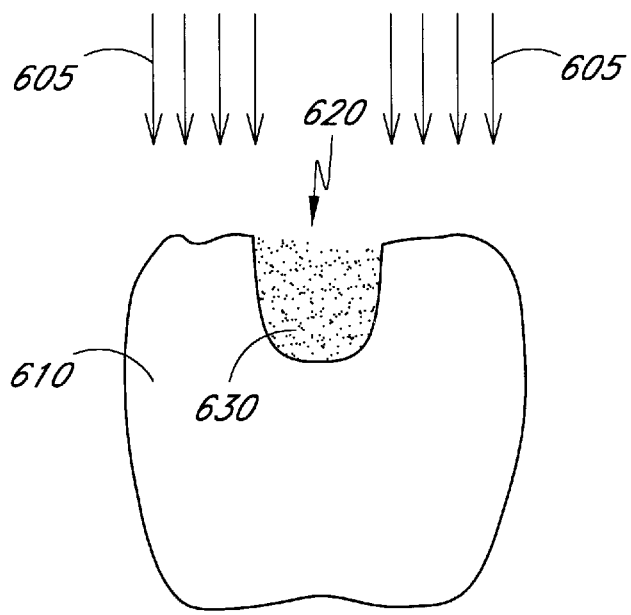
FIGS. 6A, 6B, 6C, and 6D illustrate sequentially how a composite material within a cavity in a tooth (shown in cross section) is cured so that microgaps do not form between the tooth and the cavity.
Figure 6B:
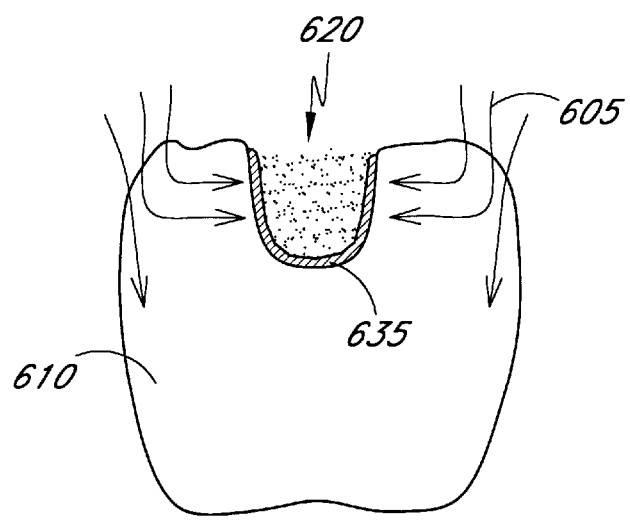

Any of these light sources 200, 200', or 200" can be advantageously used in the optical device 100 to cure dental composites, as illustrated in FIGS. 6A, B, C, and D. In FIG. 6A, an optical beam 605 having a cross section that is preferably annularly shaped is directed towards a tooth 610. (Both the beam 605 and the tooth 610 are shown in cross section.) The optical beam 605 preferably comprises blue light, as discussed earlier. The tooth 610 has a cavity 620 that is at least partially filled with a composite material 630 to be cured. As the annulus-shaped optical beam 605 strikes the tooth 610, the beam 605 is scattered within the tooth, as illustrated in FIG. 6B. As the scattered optical radiation reaches the portion of the composite material 630 that contacts the tooth 610, the composite material 630 begins to cure. A layer of cured material 635 forms at the cavity/tooth interface, whereas the composite material that is situated within the cavity 620 and away from the tooth 610 (e.g., at the center of the cavity) remains uncured.

Figure 6C:
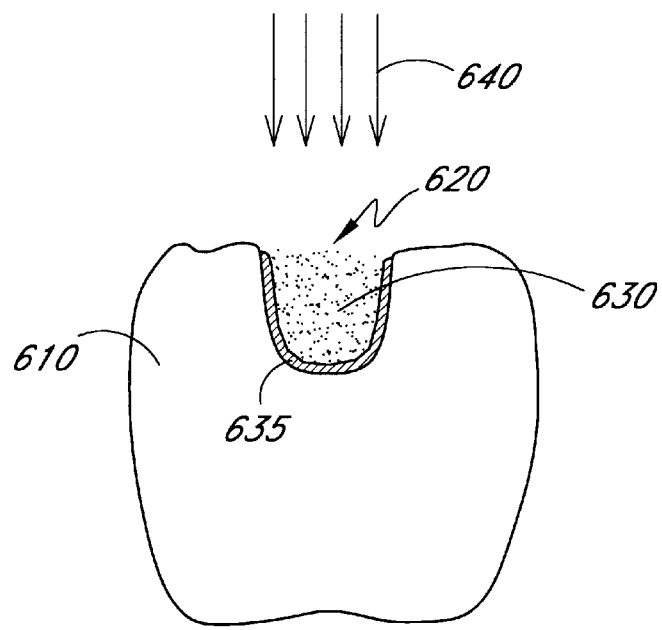
Figure 6D:
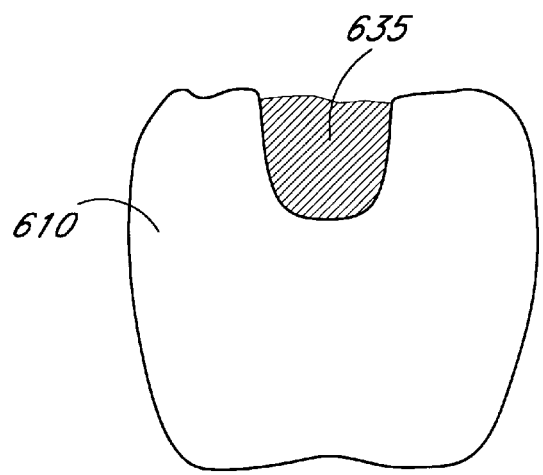

After the layer of cured material 635 has been formed, the composite material 630 that remains uncured (i.e., the composite material in the interior portion of the cavity 620) may be cured by directing a second optical beam 640 (with a cross section that is preferably circular in shape) towards the composite material within the cavity 620, as illustrated in FIG. 6C. The second optical beam 640 has a cross section that illuminates the composite material 630 more uniformly than does the first optical beam 640. For example, the second optical beam may advantageously cover the entire tooth 610, or only the cavity 620 as indicated in FIG. 6C. The remaining uncured composite material 630 (i.e., within the interior of the cavity 620) is thus cured, resulting in a cavity filled with cured composite material 635, as illustrated in FIG. 6D. The first and second optical beam patterns used in the disclosed curing method are generated upstream of the lightguide 140. It is preferable to utilize a bundle of fiber optic lightguides that have constant relative orientation throughout the length of the lightguide, so that the pattern of the beams' respective cross sections does not vary as the beams propagate through the lightguide, and so that the beams propagate along a common optical path towards the target area.

One advantage of the method discussed in connection with FIGS. 6A–D is that the formation of microgaps between the tooth 610 and the cured composite material 635 is inhibited, thereby reducing the chance that secondary caries are formed. The technique disclosed herein is a general one that can be employed to control the direction of shrinkage of light cured composite materials by suitably tailoring the pattern of the cross section of an optical beam.

As an alternative to the light source 200 directly producing optical beams with a particular shape, a wide area circular beam may be used. For example, all of the diode elements 210 or 210' may be turned on, and the optical masks 142 and 144 of FIG. 1A may be used to generate optical beams having circularly and annularly shaped cross sections, respectively. The mask 142 (or 144) may be inserted through a groove 146 in the housing 110, slipped into another groove (not shown) within the housing, and then held in place with a clip (not shown) advantageously located on the outside of the housing. In yet another embodiment, an optical beam with an annularly shaped cross section may be generated from a beam with a circularly shaped cross section (or vice versa) by using an appropriate set of optical components (such as lenses, not shown) between the diode light source 200 and the lightguide 140, in which at least one or more optical components is movable to permit the user to choose a particular pattern. Such an embodiment is necessarily longer than the one illustrated in FIG. 1A.

The optical source disclosed herein can be used in a variety of other methods, including, for example, whitening a darkened tooth or teeth. Such a method preferably comprises: preparing the teeth and gums, applying a whitening solution to the teeth, exposing the teeth to light, cleaning the exposed teeth, and exposing the cleaned teeth to one or more sodium fluoride treatments to help the teeth retain their whitened color.

First, the teeth and gums are prepared. The teeth to be whitened should be isolated from the gums and the rest of the mouth with a rubber dam which can be painted on the areas to be protected. Ligature floss or a specialty product (block out compound) can be used to form a tight cuff that will protect the gums. Each tooth should then be rubbed for about 5–10 seconds with a mixture of 35% hydrogen peroxide (or carbamide peroxide)/balance pumice, although care must be taken to avoid splattering any of this mixture into the patient's face or eyes. The teeth should not be rinsed with water after pumicing but rather wiped off with a gauze sponge.

After the teeth have been prepared, a whitening material in the form of a solution or paste should be applied to each tooth to be whitened. A variety of compounds may be used for this purpose, many of which are commercially available from firms such as Interdent (which manufactures Quaser-Brite whitening substance), Shofu (Hi-Lite and Blulite whitening substance), DenMat (QuickStart whitening substance), and LoChemCo (Varishade). Whitening materials can also be made from batch starting materials, such as hydrogen peroxide, carbamide peroxide, and silicon dioxide. The whitening material is preferably 35–50% hydrogen or carbamide peroxide. Other compounds such as silicon dioxide can be added to the peroxide to form a suspended mix or paste-like substance which has the advantage of being easy to apply.

Next, the teeth are exposed to optical radiation ("activating light"), which has the effect of accelerating the chemical reactivity of the peroxide solution. The best results are obtained if the whitening material is first allowed to seep into each tooth for a substantial period of time, e.g., at least 20–60 seconds. The source of this optical radiation is preferably a CW (continuous wave) or nearly CW laser in the optical range 400–600 nm, or more preferably 450–510 nm, i.e., optical radiation in the blue portion of the electromagnetic spectrum, such as the argon ion laser line near 488 nm, frequency doubled output from near-infrared emitting diode lasers, or the blue optical source disclosed herein. Continuous wave laser output having an average power of 300–350 mW (although satisfactory results may also be obtained over the range 100–600 mW) is preferably directed continuously for 20–40 seconds on each tooth. Laser light should not be directed to any one tooth for an arbitrary length of time, since extended exposure to laser energy heats the tooth, and vitality of the pulp is reduced if the tooth is heated too much. Preferably, the total laser energy directed to each tooth is no greater than 14 joules per application of laser energy.

After the laser treatment, the irradiated teeth should be cleaned, preferably using a water syringe. If insufficient whitening is observed, it may be desirable to repeat the whitening process by again applying whitening material to the teeth and again exposing this material to laser light. A maximum of three application/exposure cycles is preferred.

At this point, a neutral sodium fluoride gel should be applied to the teeth, with each tooth being polished with a burnishing burr, polishing cups, or discs for about 15 seconds. In addition, it is recommended that, following the treatment, the patient wear a tray with sodium fluoride suspension for about four hours on the day of the whitening procedure.

Most patients will experience a two to three shade improvement in tooth color for a single application/exposure cycle, although some patients may need to undergo the procedure two times. Regular use of a whitening tooth paste such as Colgate Platinum or Den-Mat's Rembrandt will reduce re-darkening of the teeth following the whitening procedure disclosed herein.

The optical source disclosed herein may also be used in connection with a method in which a dental composite material or a dental resin material is applied to a tooth. The array of diodes 210 may be utilized to produce activating light having a wavelength in the range 400–600 nm, and the activating light is applied to the dental composite or resin material at a power level of 100–200 mW for a period of 2–5 seconds. The activating light may be advantageously applied to the material for about 3 seconds, and the activating light is preferably applied continuously to the tooth or teeth to be treated. A power level of about 150 mW may advantageously be used.

The invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

What is claimed is:

1. A method of tooth whitening, comprising:

applying a tooth whitening material to a tooth;

allowing the tooth to be exposed to the material in the absence of activating light for a substantial period of time;

utilizing an array of diodes to produce activating light having a wavelength in the range 400 to 600 nm; and applying the activating light to the material at a power level of 100 to 600 mW for a period of 20–40 seconds.

2. The method of claim 1, further comprising terminating the application of the activating light before the tooth receives 14 Joules of laser energy during any one application of the activating light.

3. The method of claim 1, wherein the activating light has a wavelength in the range of 450–510 nm.

4. The method of claim 1, wherein the activating light is applied continuously.

5. The method of tooth whitening of claim 1, further comprising allowing the tooth to be exposed to the material in the absence of activating light for a period of time of at least about 20 seconds.

6. The method of tooth whitening of claim 1, wherein said utilizing comprises conducting electrical power to said array from a source of electrical power.

7. The method of tooth whitening of claim 1, wherein said substantial period of time is from about 20 seconds to about 60 seconds.

* * * * *